(12) United States Patent
Barneck et al.

(10) Patent No.: US 10,729,916 B2
(45) Date of Patent: Aug. 4, 2020

(54) METHODS AND APPARATUS FOR COUPLING AN ELECTROMAGNETIC RADIATION CONDUCTION SYSTEM INTO A CATHETER

(71) Applicants: Mitchell D. Barneck, Orlando, FL (US); Nathaniel L. Rhodes, Salt Lake City, UT (US); James P. Allen, Salt Lake City, UT (US); Martin de la Presa, Salt Lake City, UT (US)

(72) Inventors: Mitchell D. Barneck, Orlando, FL (US); Nathaniel L. Rhodes, Salt Lake City, UT (US); James P. Allen, Salt Lake City, UT (US); Martin de la Presa, Salt Lake City, UT (US)

(73) Assignee: Light Line Medical, Inc., Salt Lake City, UT (US)

( * ) Notice: Subject to any disclaimer, the term of this patent is extended or adjusted under 35 U.S.C. 154(b) by 156 days.

(21) Appl. No.: 15/791,574

(22) Filed: Oct. 24, 2017

(65) Prior Publication Data
US 2018/0056089 A1 Mar. 1, 2018

Related U.S. Application Data

(63) Continuation of application No. 13/801,750, filed on Mar. 13, 2013, now Pat. No. 9,808,647.
(Continued)

(51) Int. Cl.
*A61N 5/06* (2006.01)
*A61M 25/00* (2006.01)
*A61L 2/08* (2006.01)

(52) U.S. Cl.
CPC .......... *A61N 5/0624* (2013.01); *A61L 2/084* (2013.01); *A61M 25/0009* (2013.01);
(Continued)

(58) Field of Classification Search
CPC ................. A61N 5/06; A61N 5/0601; A61N 2005/0602; A61N 5/0603; A61N 2005/0604; A61N 5/0613; A61N 5/0624; A61N 2005/063; A61N 2005/0632; A61N 2005/065; A61L 2/00; A61L 2/0029; A61L 2/0052; A61L 2/0058; A61L 2/08; A61L 2/084; A61L 2/085; A61L 2/16; A61L 2/18; A61L 2202/00; A61L 2202/20;
(Continued)

(56) References Cited

U.S. PATENT DOCUMENTS 5,445,608 A * 8/1995 Chen ..................... A61N 5/0601
604/19
6,007,531 A * 12/1999 Snoke ................... A61B 1/0052
604/95.04
(Continued)

*Primary Examiner* — Ahmed M Farah
(74) *Attorney, Agent, or Firm* — Madson IP, P.C.

(57) ABSTRACT

Methods and apparatus for the inactivation of infectious agents in, on or around a catheter residing in a patient's body cavity. The method comprises a coupling adapter for facilitating the transmission of non-ultraviolet sterilizing electromagnetic radiation (EMR) substantially axially along an optical element into the catheter body. Through delivery of the sterilizing EMR to particular areas of highest infection, the present disclosure is able to inactivate the major sources of infection in catheters.

7 Claims, 6 Drawing Sheets

Related U.S. Application Data

(60) Provisional application No. 61/686,432, filed on Apr. 5, 2012.

(52) U.S. Cl.
CPC ...... *A61M 25/0017* (2013.01); *A61L 2202/24* (2013.01); *A61M 25/0028* (2013.01); *A61M 2025/0019* (2013.01); *Y10T 29/49002* (2015.01)

(58) Field of Classification Search
CPC .......... A61L 2202/24; A61L 9/00; A61L 9/18; A61L 9/20; A61L 9/205; A61M 25/0009; A61M 25/0017; A61M 25/0028; A61M 25/0029; A61M 25/003; A61M 2025/0034; A61M 2025/0019
USPC .............. 606/7, 13–18; 607/88, 89, 92, 100, 607/104–107; 422/22–24; 604/19–21, 604/27; 128/898
See application file for complete search history.

(56) References Cited

U.S. PATENT DOCUMENTS

| | | | |
|---|---|---|---|
| 7,704,247 B2* | 4/2010 | Soltz | A61B 18/22 606/13 |
| 8,706,211 B2* | 4/2014 | Dacey, Jr. | A61F 2/30 604/20 |
| 2013/0023770 A1* | 1/2013 | Courtney | A61B 1/0016 600/467 |

\* cited by examiner

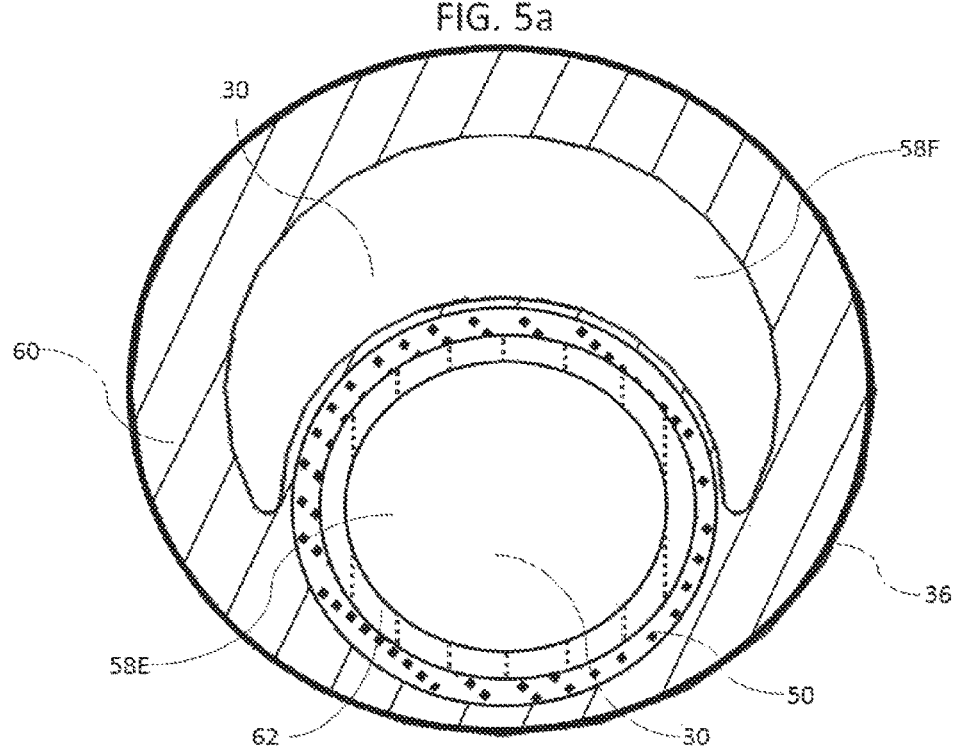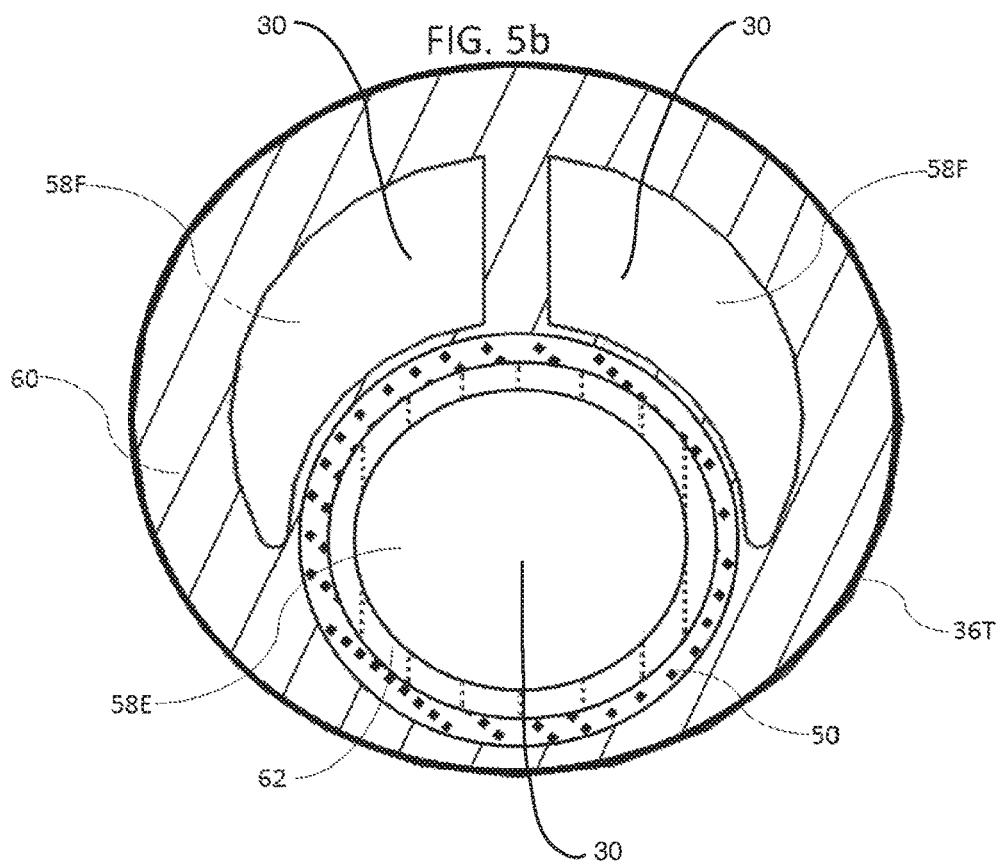

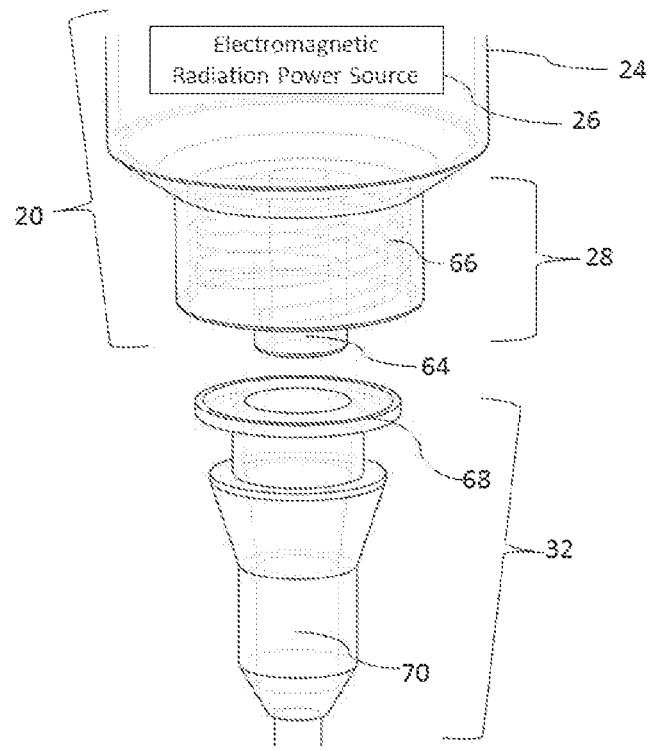
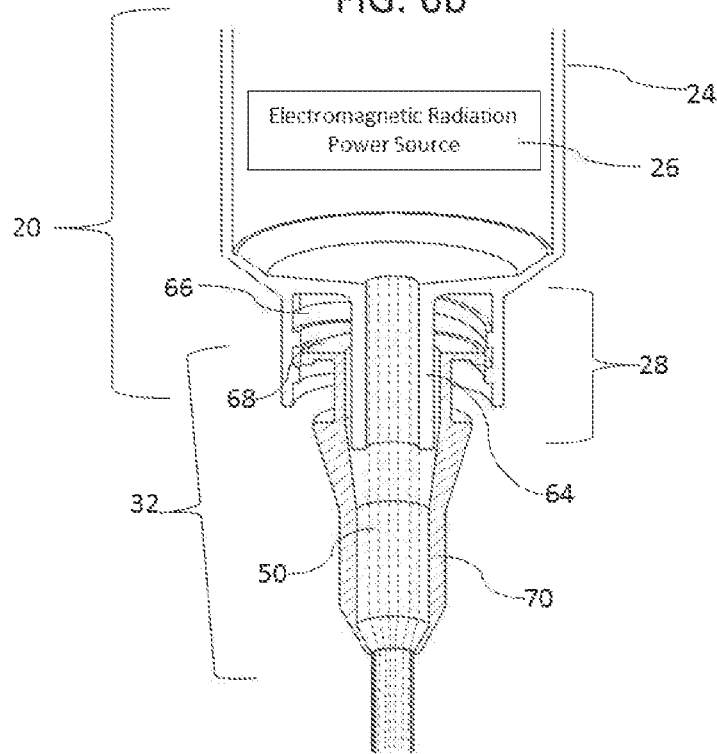

METHODS AND APPARATUS FOR COUPLING AN ELECTROMAGNETIC RADIATION CONDUCTION SYSTEM INTO A CATHETER

RELATED APPLICATION

This application is a continuation of U.S. patent application Ser. No. 13/801,750, filed on Mar. 13, 2013 and entitled METHODS AND APPARATUS TO INACTIVATE INFECTIOUS AGENTS ON A CATHETER RESIDING IN A BODY CAVITY. This application also claims the benefit of U.S. Provisional Application No. 61/686,432 filed Apr. 5, 2012, for an invention titled HINS LASER LIGHT CATHETER. Both of the above-referenced applications are incorporated by this reference as if fully set forth herein.

TECHNICAL FIELD

This disclosure generally relates to methods and apparatuses to inactivate infectious agents on a catheter while residing in a patient's body cavity. In particular, the disclosure is a medical device assembly that utilizes non-ultraviolet sterilizing electromagnetic radiation (EMR) at a high enough intensity to reduce or eliminate infectious agents in, on, and around a catheter while it resides inside a body cavity.

BACKGROUND

Catheters are commonly used as channels to inject medications or retrieve fluid samples in a patient. Each catheter comprises a tube, usually derived from plastic or other polymers, such as silicone, polyurethane, and the like, that is inserted into an area of the body and may contain one or more separate lines in which these fluids may be delivered or retrieved. A "lumen" designates a pathway in the catheter that goes from outside the body to inside the body. Catheters are used in various applications, including intravascularly, urologically, gastrointestinally, ophthalmically, within the respiratory tract, within the cranial space, within the spinal column, and the like. In all cases, the catheter is placed inside of a space in the body where the catheter resides, herein referred to as a "body cavity". These devices frequently give rise to infections caused by growth of infectious agents in, on, and around the catheter. Infectious agents can include bacteria, fungi, viruses, or the like that enter the body and lead to illness of a patient. Depending on the location of the catheter placement, these infections can arise in the form of urinary tract infections, blood stream infections, soft tissue infections, and the like.

Catheter related infections (CRIs) are a large problem in medicine, leading to high morbidity and mortality rates. Current methods of reducing or eliminating the number of infectious agents in and on a catheter are of low efficacy. Typically, catheters will be removed if they are suspected to be harboring infectious agents, increasing both the cost associated with treatment and patient discomfort. Various methods to deter or eliminate growth of infectious agents in catheters have been attempted, such as using sterile handling techniques, antibiotics, and replacing the catheter when an infection is suspected. Despite these techniques, infections resulting from catheters remain a major problem. According to the Centers for Disease Control and Prevention, over 31,000 people died specifically from catheter-related bloodstream infections in 2010. These infections, along with urinary tract infections, gastrointestinal infections, and other infections from catheters, increase both medical costs and patient discomfort.

The use of ultraviolet (UV) light, disinfecting chemicals, catheters impregnated with drugs, to name a few, have been attempted to reduce the prevalence of infection. Many patents have attempted to utilize UV light to disinfect catheters. Unfortunately, UV light is well known to cause damage to living cells. Methods to disinfect connectors, stopcocks, and valves using sterilizing electromagnetic radiation (EMR) have also been attempted using 405 nm light to sterilize these points, but these methods neglect disinfection of the catheter body as well as the tip of the catheter.

The emergence of infectious agents that are resistant to current treatments, such as methicillin-resistance *Staphylococcus aureus* (MRSA), further substantiate the need for another treatment of CRIs. To reduce the cost associated with having to remove the catheters from the patient, there is a need for a catheter that can be sterilized while residing in the patient.

Additionally, immediate disinfection after placement could help prevent the growth of biofilm on the catheter. Biofilm consists of extracellular polymeric material created by microorganisms after they adhere to a surface. This biofilm facilitates the growth of infectious agents and is very difficult to break down once it has begun to grow.

The growth of infectious agents can result from agents outside the patient (at the point of access as the catheter crosses the skin or from the catheter hub) or from inside the patient, wherein infectious agents that enter the body attach to the surface of the catheter and proliferate. Scientific literature suggests that approximately 65% of CRI's come from infectious agents residing on the skin of the patient (S. Öncü, Central Venous Catheter—Related Infections: An Overview with Special Emphasis on Diagnosis, Prevention and Management. The Internet Journal of Anesthesiology. 2003 Volume 7 Number 1). These agents travel down the outside of the catheter and colonize the catheter tip. For short term catheterization, this is believed to be the most likely mechanism of infection (Crump. Intravascular Catheter-Associated Infections. Eur J Clin Microbiol Dis (2000) 19:1-8). Thirty percent (30%) of CRIs are believed to come from a contaminated hub, in which infectious agents travel down the interior of the catheter (Öncü). This is believed to be the most likely mechanism of infection for long-term catheterization (Crump).

EMR in the range of 380-900 nm has been shown to be effective in killing infectious agents. Research shows that light in this range is effective in killing surface bacteria in burn wards without harming the patients (Environmental decontamination of a hospital isolation room using high-intensity light. J Hosp Infect. 2010 November; 76(3):247-51). Published patent application 2010/0246169, written by the members who conducted the study, utilizes ambient lighting to disinfect a large surrounding area. The mechanism proposed by the team suggests that light in this range leads to photosensitization of endogenous porphyrins within the bacteria, which causes the creation of singlet oxygen, leading to the death of the bacteria. (Inactivation of Bacterial Pathogens following Exposure to Light from a 405-Nanometer Light-Emitting Diode Array. Appl Environ Microbiol. 2009 April; 75(7):1932-7).

Heretofore, however, there has never been apparatuses or methods for making or using such apparatuses to safely and effectively disinfect a catheter while it is still implanted in a patient.

SUMMARY OF THE INVENTION

This disclosure relates to a medical device assembly for insertion into a cavity of a patient's body and for delivery and retrieval of fluids. The assembly comprises an electromagnetic radiation (EMR) source for providing non-ultraviolet, sterilizing EMR having intensity sufficient to inactivate one or more infectious agents. This catheter has an elongate catheter body with at least one internal lumen, a coupling end, and a distal end tip. This distal end tip is insertable into the cavity of the patient's body, wherein the catheter body directs both the fluid and the sterilizing EMR axially through the catheter body for delivery into the patient's body at the distal end tip. An optical element disposed within the catheter body acts conducive to the axial propagation of the sterilizing EMR through the catheter body. The optical element or another optical element also may be disposed to act conducive to propagation of sterilizing EMR through at least one coupling element to connect the EMR component to the insertable catheter component.

This disclosure also provides methods and apparatuses for effectively sterilizing a catheter and the surrounding area while in a body cavity. This medical device assembly uses sterilizing EMR to reduce or eliminate the count of infectious agents in, on, or around the catheter while in a body cavity.

This disclosure also relates to a medical device assembly for insertion of a catheter into a cavity of a patient's body, for delivery to and retrieval of a fluid from the patient's body, comprising an EMR source. This source can be from a group of EMR sources including a solid state laser, a semiconductor laser, a diode laser, and a light emitting diode. This EMR source provides non-ultraviolet, sterilizing EMR having a wavelength in the range of approximately 380 nm to approximately 900 nm and has an intensity sufficient to inactivate one or more infectious agents.

This disclosure describes a catheter having an elongate catheter body with at least one internal lumen, a coupling end and a distal end tip, the distal end tip being insertable into the cavity of the patient's body. The catheter body is meant to direct both the fluid and the sterilizing EMR axially through the catheter body for delivery into the patient's body at the distal end tip. This disclosure includes an optical element disposed within the catheter body and conducive to the axial propagation of the sterilizing EMR through the catheter body. Finally, this disclosure describes at least one coupling element to connect the radiation source to the catheter body.

The sterilizing EMR is transmitted down a specialized path within the catheter via an optical element conducive to the axial propagation of the light. Various methods could be used to facilitate propagation of the light down the catheter, including a reflective coating within a line of the catheter, a fiber optic cable, a lens, a waveguide, or the like. The light source can be a light-emitting diode (LED), laser, fiber optic filament, or the like.

Of particular interest to this medical device assembly is the use of light between 380 and 900 nm wavelengths. Additionally, the intensity and power of the light emitted is important for the inactivation of infectious agents, thus a range of intensities covering 0.1 J/cm2 to 100 J/cm2 and a range of powers from 0.005 mW to 1 W is of interest for these device assemblies and methods.

For each exemplary embodiment, the medical device assembly and method for disinfection could be utilized in an adjustable duty cycle. If treatments began immediately after insertion of the device, catheter biofilm growth may be inhibited.

This disclosure also relates to a method for constructing a medical device assembly for insertion into a cavity of a patient's body and for delivery of a fluid to the patient's body comprising the steps of: providing a catheter having an elongate catheter body with at least one internal lumen, a coupling end and an distal end tip, the distal end tip being insertable into the cavity of the patient's body; applying an optical element within the catheter body, the optical element being conducive to the axial propagation of a sterilizing EMR through the catheter body; and coupling an EMR source to the catheter body, the EMR source for providing non-ultraviolet, sterilizing EMR having an intensity sufficient to inactivate one or more infectious agent.

In one exemplary embodiment, the device uses a catheter that is inserted into a cavity of a patient's body, wherein said catheter allows both fluid and sterilizing EMR to travel axially through the catheter body. The catheter also contains at least one coupling lumen to connect an EMR sterilization source that will transmit the EMR through the coupling lumen and down through the catheter line. A coupling element in this context will usually refer to a typical hub on the sterilizing EMR source.

In another exemplary embodiment, a catheter with multiple lumens for fluid injection or retrieval contains a separate lumen for transmission of the sterilizing EMR. Each lumen has a separate proximal catheter hub assembly. These internal lumens converge at a convergence chamber, where individual internal lumens consolidate into a single elongated catheter body while retaining their individual internal paths. This device may include use of an optical method for diverting the radiation between the convergence chamber and axially through the designated catheter internal lumen.

Samples from the distal end tip are often used to characterize the type of infection. One embodiment of the disclosure focuses on maintaining full internal reflection of the light down the catheter and delivering the light to the distal end tip of the catheter to reduce or eliminate the count of infectious agents residing thereon.

In yet another exemplary embodiment, the medical device assembly aforementioned would be used in a urological setting. The catheter would be placed into the urethra and bladder of the urinary tract.

In yet another exemplary embodiment, the medical device assembly aforementioned would be used in a gastrointestinal setting.

In yet another exemplary embodiment, the medical device assembly aforementioned would be used in an intravascular setting.

In yet another exemplary embodiment, the medical device assembly aforementioned would be used within the cranial cavity of a patient.

In yet another exemplary embodiment, the medical device assembly aforementioned would be used within the spinal cavity of a patient.

In still another exemplary embodiment, the medical device assembly aforementioned would be used within an ophthalmic cavity of a patient.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the present disclosure will be described with additional specificity and detail through use of the accompanying drawings in which:

FIG. 5a is a cross sectional view of an alternate embodiment showing a double lumen line with a reflective surface to allow reflective axial propagation of EMR;

FIG. 5b is a cross sectional view of an alternate embodiment showing a triple lumen line with a reflective surface to allow reflective axial propagation of EMR;

FIG. 6a is an exploded perspective view of the catheter hub and coupling element;

FIG. 6b is a cross sectional view of the catheter hub and laser port assembly of FIG. 6a;

DETAILED DESCRIPTION

Exemplary embodiments of the present disclosure will be best understood by reference to the drawings, wherein like parts are designated by like numerals throughout. It will be readily understood that the components of the exemplary embodiments, as generally described and illustrated in the Figures herein, could be arranged and designed in a wide variety of different configurations. Thus, the following more detailed description of the embodiments of the apparatus, system, and method of the present disclosure, as represented in FIGS. 1 through 9, is not intended to limit the scope of the invention, as claimed, but is merely representative of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
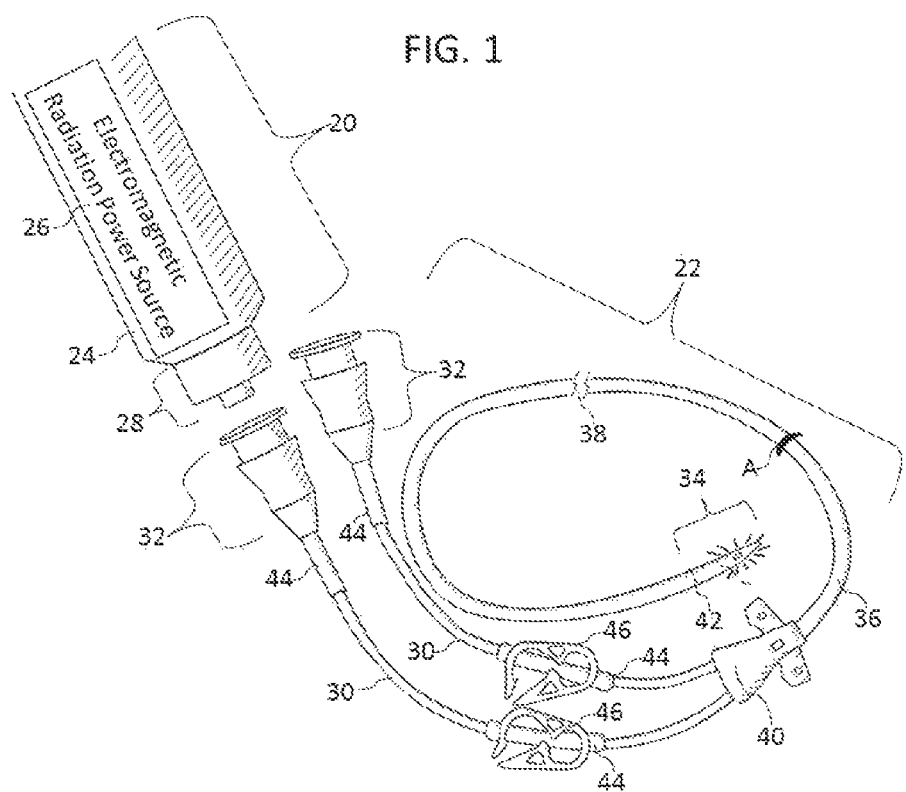
FIG. 1 is a perspective view of a double lumen catheter and an EMR component.

Referring now to FIG. 1 of the present disclosure, a medical device assembly comprises a non-ultraviolet, electromagnetic radiation (EMR) component 20, and an insertable catheter component 22. The non-ultraviolet, EMR component 20 broadly comprises an elongate body 24 used to enclose the EMR power source 26 and a coupling element 28 to couple the two components of the assembly. The EMR shall be defined as electromagnetic radiation (EMR) manifested as light emitted in a range from 380 nm to 900 nm having a high intensity sufficient to inactivate one or more infectious agents. In some embodiments, the EMR source has an adjustable duty cycle length so that the EMR can be provided at the most effective times and for beneficial time periods.

Additionally, although a wavelength in a range from 380 nm to 900 nm with a sufficient intensity will inactivate one or more infectious agents, more precise wavelengths may have more particular efficacy against certain infectious agents or for a desired purpose. It has been determined that sterilizing EMR of wavelengths including wavelengths centered about 400 nm, 405 nm, 415 nm, 430 nm, 440 nm, 455 m, 470 nm, 475 nm, 660 nm, and 808 nm have particular efficacy.

The insertable catheter component 22, being capable of at least partially being inserted into a cavity of the patient's body to deliver the non-ultraviolet EMR, comprises of at least one internal lumen 30, a proximal catheter hub assembly 32, and a distal end tip 34. An internal lumen 30 being simply defined as the internal path by which fluid or EMR may travel. In cases of a single or multi-lumen catheter, similar features in the drawings will be labeled with the same number.

The distal end tip 34 being insertable into the cavity of the patient's body at a determined site A, wherein the elongate catheter body 36 directs both the fluid and the sterilizing EMR axially through the elongate catheter body 36 for delivery into the patient's body at the distal end tip 34. The elongate catheter body is described as being an elongated catheter having at least one internal lumen.

Sterilizing EMR will travel axially through the catheter which may be of varying lengths 38 depending on its specific need. The fluid used through the internal lumen 30 is generally configured to contain pharmacological compounds (e.g., a drug) or biological fluids (e.g., blood, urine, or cerebral spinal fluid).

The embodiment shown contains two lumens 30, and proximal catheter hub assemblies 32. Each may be used to direct fluid or the sterilizing EMR axially through the elongate catheter body 36 depending on the specific needs of the catheter. In multi-lumen embodiments, a dedicated single lumen may also be designated for the axial propagation of EMR and each additional lumen dedicated for the propagation of fluid axially. In this way both fluid and EMR can be axially propagated simultaneously through their individual lines.

This figure depicts a multi-lumen embodiment of the disclosure. Each multi-lumen embodiment may contain a convergence chamber 40, at the point where individual internal lumens 30 converge into a single elongated catheter body 36 while retaining their individual internal paths. At the distal end tip 34 of the elongate catheter body 36, the optical element 50 (shown best in FIG. 4) discontinues at the termination point 42 so that the sterilizing EMR can irradiate throughout the tip and surrounding cavity area.

This embodiment also is fitted with flexible protection tubing 44 to protect the lumen at the proximal catheter hub assembly 32 and between the proximal catheter hub assembly 32 and convergence chamber 40. If manual line occlusion is necessary it may be performed with the line clamp 46.

Figure 2:
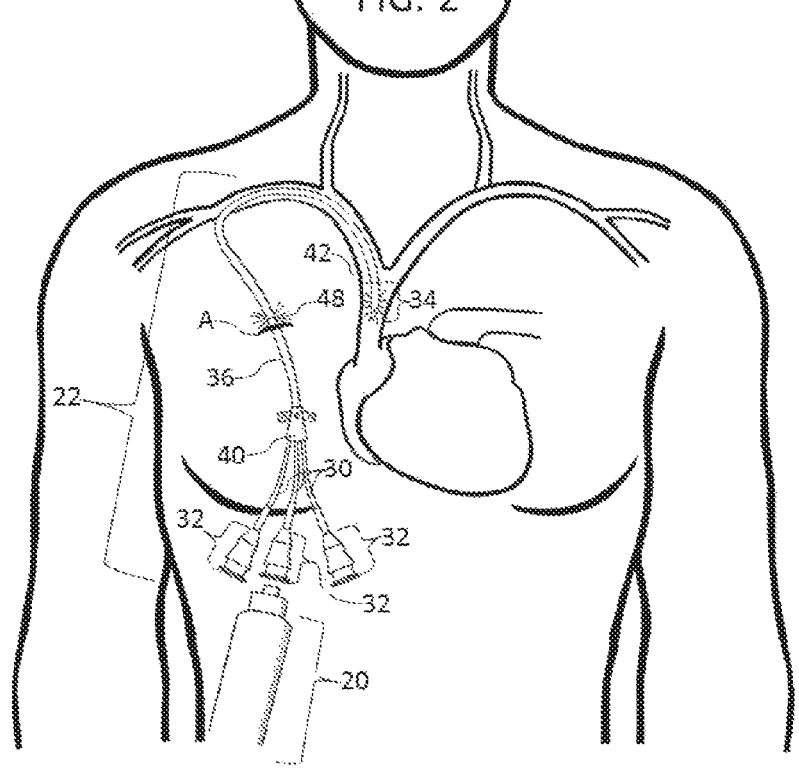
FIG. 2 is a schematic view of a tunneled triple lumen catheter embodiment as inserted into a body cavity.

Referring now to FIG. 2 of the present disclosure, a schematic view of another embodiment of the medical device assembly comprises a non-ultraviolet, EMR component 20, and an insertable catheter component 22. The embodiment shown is specifically a tunneled triple lumen central line variation of the disclosure; however it should be understood that the catheter may encompass any type of accessing catheter (e.g., vascular, gastrointestinal, etc.) without departing from the scope and spirit of the invention. The non-ultraviolet EMR component 20 is coupled to the proximal catheter hub assembly 32 of the insertable catheter component 22. The other coupling hubs 32 are available for axial propagation of fluid. Each designated internal lumen 30 propagates the EMR or fluid between its proximal catheter hub assembly 32 and distal end tip 34.

The transcutaneous portion A of the insertable catheter body 36 is often a high source of infections. To reduce infections at this point, a dedicated area 48 is a region free from the optical element 50 within the elongate catheter body 36. This allows the sterilizing EMR to irradiate outward and inactivate the infectious agents at the insertion site A.

At the distal end tip 34 of the elongate catheter body 36, the optical element 50 discontinues at the termination point 42 so that the sterilizing EMR can irradiate throughout the tip and surrounding cavity area.

Figure 3:
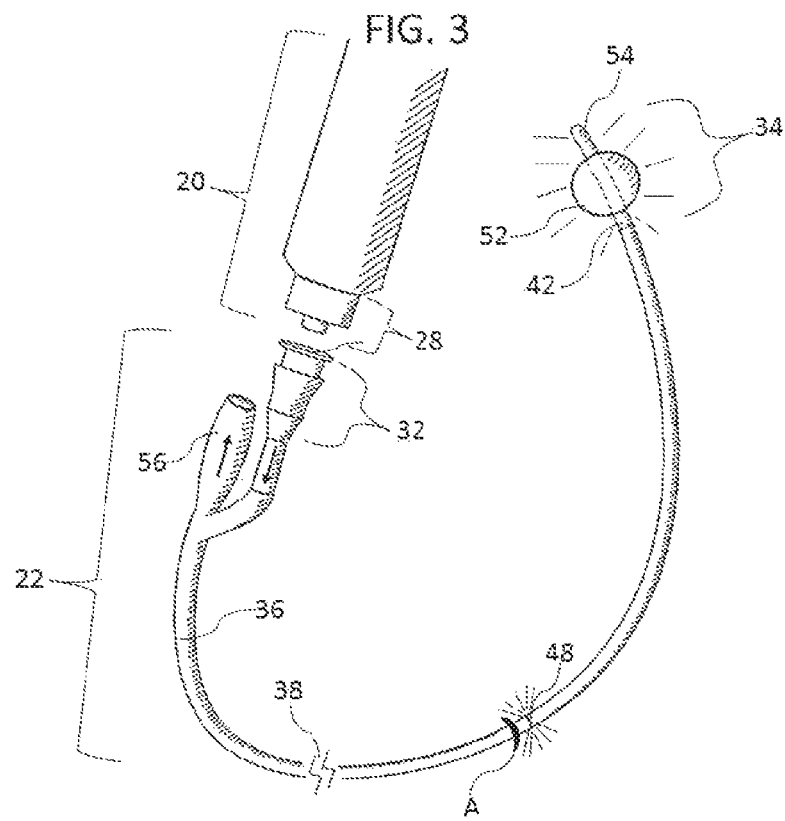
FIG. 3 is a perspective view of an alternative embodiment showing a urinary catheter.

Referring now to FIG. 3 of the present disclosure, a perspective view of yet another exemplary embodiment of the medical device assembly comprises a non-ultraviolet, EMR component 20, and an insertable catheter component 22. The exemplary embodiment shown is specifically an indwelling urinary balloon catheter variation; however, it should be understood that catheter may also encompass any type of drainage catheter (e.g., urinary, fecal, cranial, or spinal). The EMR component 20 is connected at the coupling element 28 to the proximal catheter hub assembly 32 of the insertable catheter component 22. Fluid delivery from the proximal catheter hub assembly 32 to the distal end tip 34 may also be made through the proximal catheter hub assembly 32. Sterilizing EMR will travel axially through the indwelling catheter, which may be of varying lengths 38 depending on its specific need.

The transcutaneous portion A of the insertable catheter body 36 is often a high source of infections. To reduce infections at this point, a dedicated area 48 is a region free from the optical element 50 within the elongate catheter body 36, thereby allowing the sterilizing EMR to irradiate outward and inactivate the infectious agents at the insertion site A.

This exemplary embodiment of the disclosure is shown having an inflatable balloon 52 to assist in securing the elongate catheter body 36 in the desired location within the patient's body. Once the elongate catheter body 36 is disposed within the patient's body, the inflatable balloon 52 may be inflated through the addition of fluid through the proximal catheter hub assembly 32.

At the distal end tip 34 the elongate catheter body 36 is free of the optical element 50. The termination point of the optical element 42 allows the sterilizing EMR to irradiate throughout the distal end tip 34 and surrounding cavity area.

Drainage occurs from the distal end tip fluid exposure site 54 through the elongate catheter body 36 and out of the drainage hub 56. The drainage hub 56 can be connected to a variety of containers for storage or disposal of the draining fluid based on the needs of the embodiment.

Figure 4:
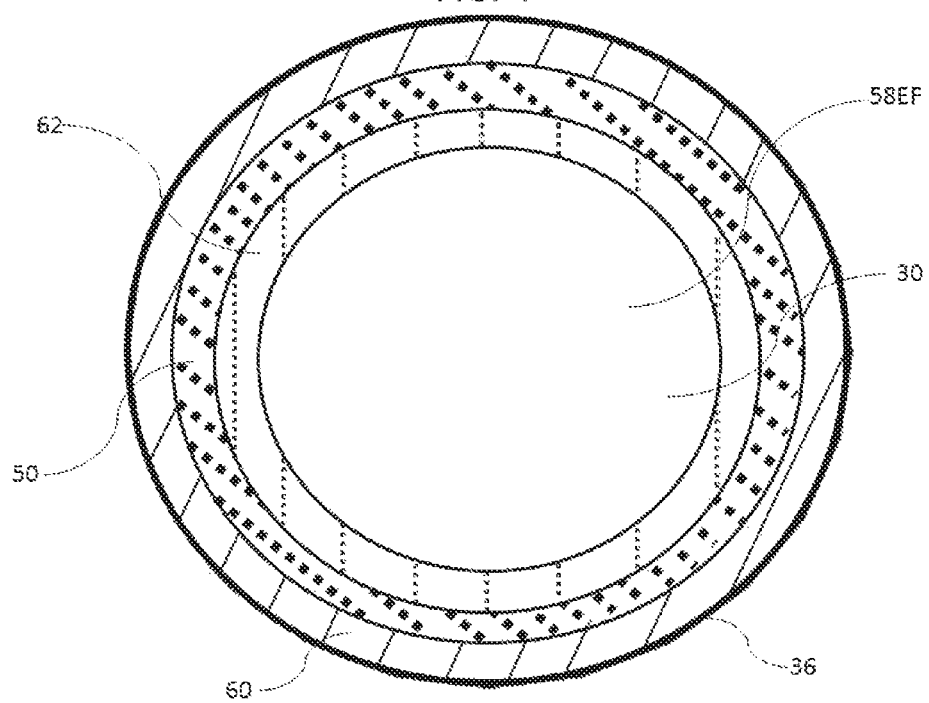
FIG. 4 is a cross sectional view of an exemplary embodiment of a single lumen with a reflective surface to allow reflective axial propagation of EMR.

Referring now to FIG. 4 of the present disclosure, a cross-sectional view of an exemplary embodiment of a single lumen elongate catheter body 36 is shown. Through the internal lumen 30, the sterilizing EMR and fluid element 58EF travels axially. The numbering is such that the letter "E" is representative of the transmission of EMR and the letter "F" is representative of the transmission of fluid. This numbering convention will be continued hereafter. The layers comprise an outer layer 60 which would come into contact with a patient's cavity walls, an optical element layer 50 to assist in the axial propagation of EMR through the elongate catheter body 36, and a translucent layer 62 which comes into contact with the EMR and the fluid.

The elongate catheter body 36 of the present exemplary embodiment has a single internal lumen 30 and is a desirable option in areas where multiple lumens are not possible, e.g., narrow cavities, in children.

The optical element 50 can be manufactured using a broad range of reflective technologies. The most common known would include, individually or in combination, at least one of a metallic coating, reflective coating, reflective plating, vapor deposited layer, coextruded metallic particle layer, a coextruded reflective layer, reflective film, and embedded metallic resin. It is desirable for the catheter to be both sterilize-able and feasible to use in a living patient. Therefore, all other methods which deposit or embed a reflective surface on an elongate catheter body 36 and allow for a safe and effective transmission of sterilizing EMR down the length of the catheter substantially axially are also contemplated. In areas of the elongate catheter body 36 that are desirable to have the sterilizing EMR irradiate the surrounding tissue and not propagate the length of the catheter axially, the optical element 50 may be removed. In the present disclosure, these areas include: inside the convergence chamber 40, at the insertion site A, and at the distal end tip 34. In embodiments in which the optical element 50 may come in contact with the patient's body cavity, the outer layer 60 may be removed.

Referring now to FIG. 5a of the present disclosure, a cross-sectional view of another exemplary embodiment of a double lumen elongate catheter body 36 is shown. Through the internal lumen 30, the fluid element 58F travels axially. Through the internal lumen 30, the sterilizing EMR element 58E may also travel axially. The sterilizing EMR element 58E and the fluid element 58F retain their own individual lumens to travel through. In some embodiments, the optical element 50 may also be embedded in the catheter body 36 so that it surrounds the fluid element 58F. The layers comprise an outer layer 60 which would come into contact with a patient's cavity walls, an optical element layer 50 to assist in the substantial axial propagation of EMR through the elongate catheter body 36, and a translucent layer 62 which may contact the EMR and the fluid. For purposes of this application, "substantial axial propagation of EMR" means that EMR advances along a generally axial path proximate the longitudinal axis of the catheter, though the path need not be linear or sinusoidal.

The elongate catheter body 36, as a double internal lumen 30 embodiment, is a desirable option in areas where drainage of fluid may be necessary (e.g., urinary catheters, cranial catheters, spinal catheters, fecal catheters, and the like).

The optical element 50 can be manufactured using a broad range of reflective technologies. The most common would include: a metallic coating, reflective coating, reflective plating, vapor deposited layer, co-extruded metallic particle or reflective layer, reflective film and embedded metallic resin. It is desirable for the catheter to be both sterilize-able and feasible to use in a living patient. All additional methods for assisting in the substantial propagation of EMR using a reflective surface for the effective transmission of sterilizing EMR are also contemplated. In areas of the elongate catheter body 36 that are desirable to have the sterilizing EMR irradiate the surrounding tissue and not propagate the length of the catheter axially, the optical element 50 may be removed. In the present disclosure, these areas may include: inside the convergence chamber 40, at the insertion site A, and at distal end tip 34. In certain embodiments which the optical element 50 may come in contact with the patient's body cavity, the outer layer 60 may be removed.

FIG. 5b shows a cross-sectional view of the exemplary embodiment of a multi-lumen elongate catheter body 36. Through the internal lumen(s) 30, the fluid element 58F or multiple fluid elements 58F may travel axially. Through the internal lumen 30, the sterilizing EMR element 58E may also travel axially. The sterilizing EMR element 58E and the fluid element 58F retain their own individual lumens to travel through. In some embodiments the optical element 50 may also be embedded in the catheter body 36 so that it surrounds the fluid element 58F. The layers comprise an outer layer 60 which would come into contact with a patient's cavity walls, an optical element layer 50 to assist in the substantial axial propagation of EMR through the elongate catheter body 36, and a translucent layer 62 which comes into contact with the EMR. In certain embodiments in which the optical element 50 may come into contact with the patient's body cavity, the outer layer 60 may be removed.

The elongate catheter body 36 of FIG. 5b is a triple lumen embodiment and may be a desirable option in areas where multiple fluid delivery or extraction is necessary simultaneously. In hemodialysis, venous and arterial blood is exchanged simultaneously. This exemplary embodiment would allow for the necessary function of the catheter to continue as desired.

FIG. 6a of the present disclosure is an exploded view of the EMR component 20 and the proximal catheter hub assembly 32. The EMR component 20 comprises an elongate body 24 used to enclose the EMR power source 26 as well as a coupling element 28 to couple the two components of the assembly. The coupling element 28 shown comprises two parts, an inner male component 64 and an outer threaded male component 66. The inner male component 64 is designed to both align with and recess into the catheter hub assembly 32, thereby giving an aligned union between the coupling element 28 and the catheter hub assembly 32, as well as ensuring a minimal amount of EMR is lost by escaping the catheter hub assembly 32. The outer threaded component 66 has a threaded region which can be used to fasten itself to the catheter hub female coupling 68 by rotating onto it. It should be understood that for some embodiments, it may be advantageous to implement a focusing lens to focus the EMR for more effective axial propagation. A person of skill in the art, armed with this disclosure, could effectively implement a focusing lens.

The proximal catheter hub assembly 32 comprises a catheter hub female coupling 68 and an elongated hub body 70. The internal wall of the elongated hub body 70 also may be coated with an optical element 50.

Referring now to FIG. 6b of the present disclosure, a cross-sectional view of the EMR component 20 and the proximal catheter hub assembly 32 is shown. The EMR source comprises an elongate body 24 used to enclose the EMR power source 26 and a coupling element 28 to couple the two components of the assembly. The coupling element 28 shown comprises two parts, an inner male component 64 and an outer threaded male component 66. The inner male component 64 is designed to both align with and recess into the proximal catheter hub assembly 32, thereby giving an aligned union between the coupling element 28 and the proximal catheter hub assembly 32 as well as ensuring a minimal amount of EMR is lost by escaping from the proximal catheter hub assembly 32. The outer threaded male component 66 has a threaded region, which can be used to fasten itself to the catheter hub female coupling 68 by rotating onto it.

The proximal catheter hub assembly 32 comprises a catheter hub female coupling 68 and an elongated hub body 70. The internal wall of the elongated hub body 70 also may be coated with an optical element 50.

Figure 7A:
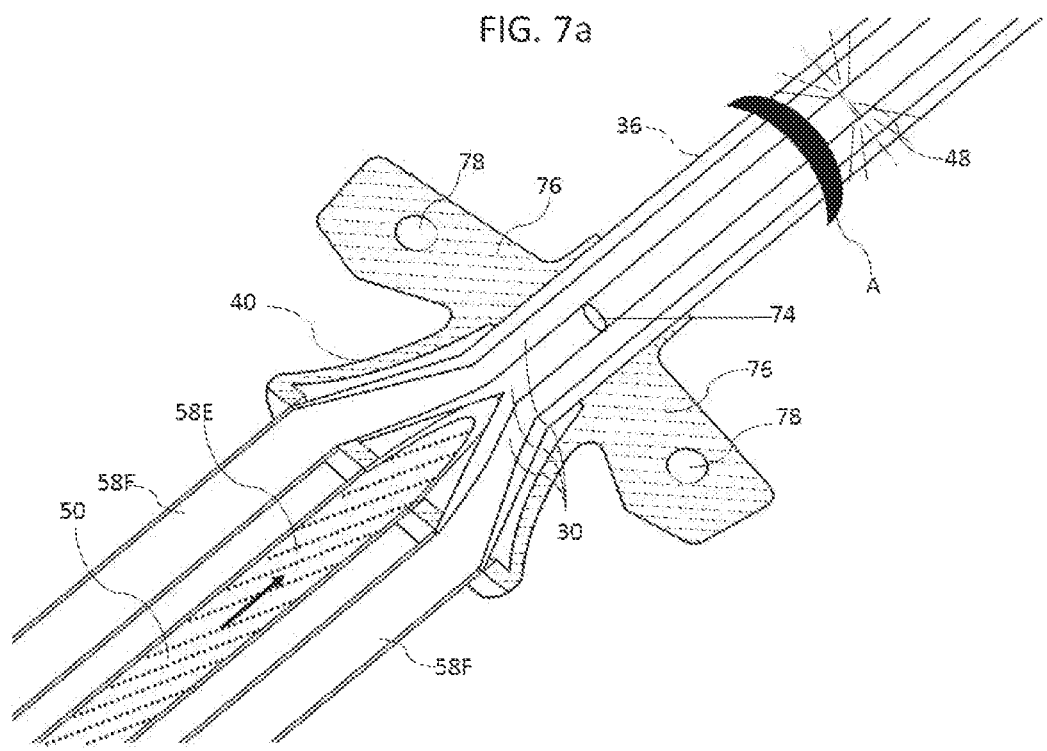
FIG. 7a is a cross sectional view of an exemplary embodiment showing inbound lines into a convergence chamber.

Referring now to FIG. 7a of the present disclosure, a cross-sectional view of a triple internal lumen 30 embodiment shows fluid elements 58F and an EMR element 58E joining into the convergence chamber 40 and leaving as a single elongate catheter body 36 while retaining individual paths.

The convergence chamber 40 contains an adjustable optical diversion element assembly 74 which will redirect EMR from the electromagnetic power source 26 into at least one of the internal lumens 30 containing a fluid element 58F. If desired, sterilizing the fluid which may travel through the fluid element 58F may be accomplished by reflecting at least a portion of the EMR back up the individual feed lines. In some embodiments the optical element 50 may also be embedded in the catheter body 36 so that it surrounds the fluid element 58F. In this way, the optical element 50 is able to sterilize the length of the fluid line axially from the proximal catheter hub assembly 32 to the distal end tip 34. The convergence chamber 40 contains attachment arms on either side 76 to assist in securing to the patient. If suturing or additional support is necessary there are specialized holes 78 in the attachment arms, which allow a point to fasten to.

The transcutaneous portion A of the insertable catheter body 36 is often a high source of infections. To reduce infections at this point, a dedicated transcutaneous area 48 is a region free from the optical element 50 within the catheter body 36, thereby allowing the sterilizing EMR to irradiate outward and inactivate the infectious agents at the insertion site A.

Figure 7B:
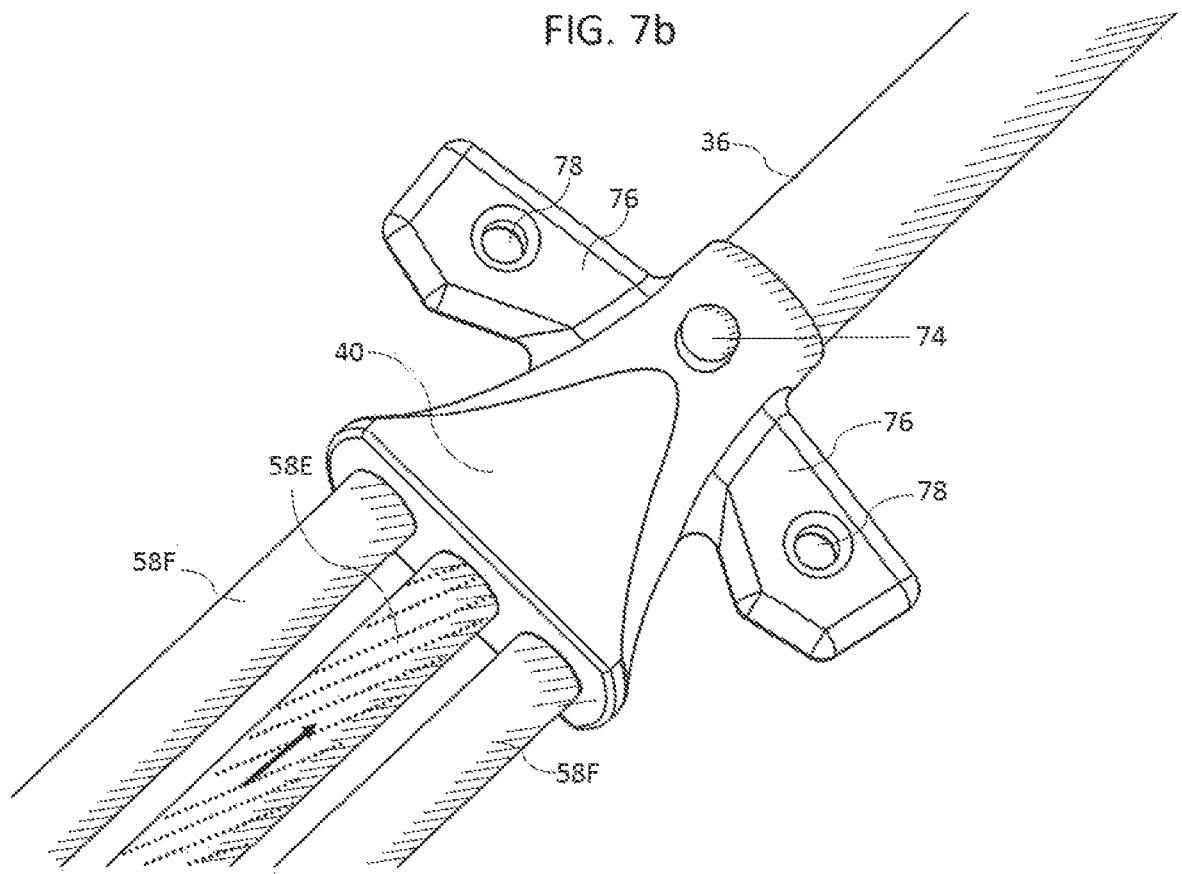
FIG. 7b is a perspective view of an exemplary embodiment showing inbound lines into a convergence chamber.

Referring now to FIG. 7b of the present disclosure, a profile view of a triple internal lumen 30 embodiment shows fluid element 58F and an EMR element 58E joining into the convergence chamber 40 and leaving as a single elongate catheter body 36 while retaining individual paths.

The convergence chamber 40 may contain an adjustable optical diversion element assembly 74 which will redirect EMR from the electromagnetic power source 26 into at least one of the internal lumens 30 containing a fluid element 58F, thereby sterilizing the fluid which may travel through the fluid element 58F. The convergence chamber 40 has attachment arms on either side 76 to assist in securing itself to the patient. If suturing or additional support is necessary there are specialized holes 78 in the attachment arms, which allow a point to fasten to.

Figure 8:
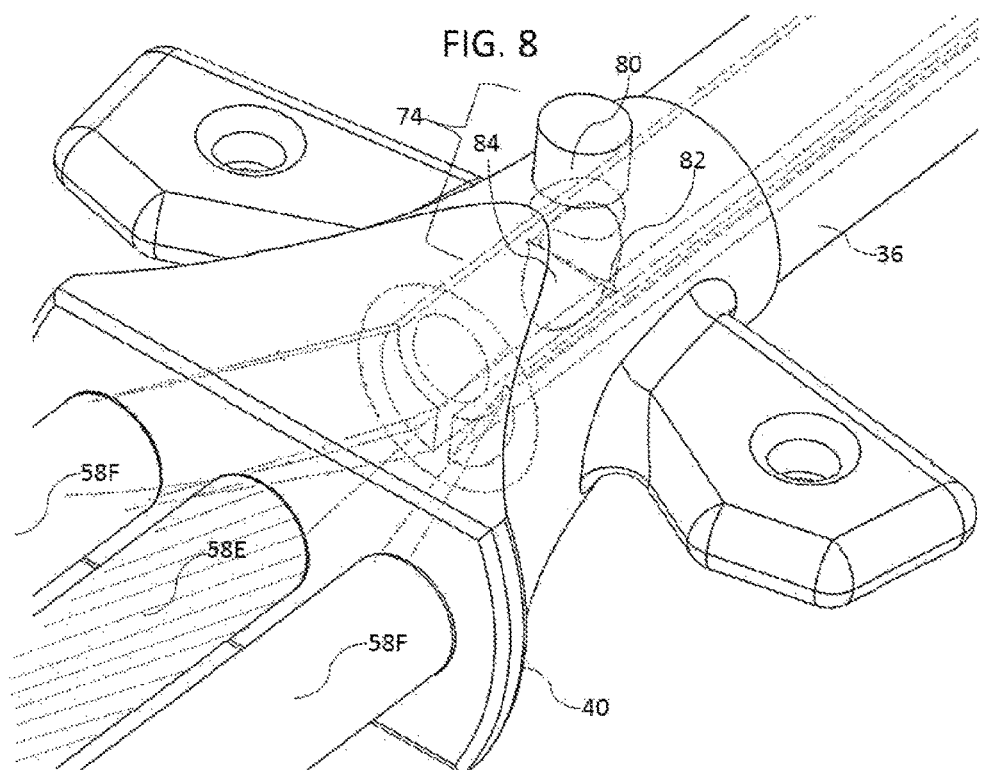
FIG. 8 is a convergence chamber perspective view showing internal configuration in phantom lines.

In FIG. 8, a perspective view is provided of a triple lumen embodiment with internal phantom lines showing fluid lines 58F and an EMR line 58E joining into the convergence chamber 40 and leaving as a single elongate catheter body 36 while retaining individual paths.

The convergence chamber 40 may contain an adjustable optical diversion element assembly 74 which will redirect EMR from the electromagnetic power source 26 into at least one of the internal lumens 30 containing a fluid element 58F. In some embodiments the optical element 50 may also be embedded in the catheter body 36 so that it surrounds the fluid element 58F. In this way, the optical element 50 is able to sterilize the length of the fluid line axially both to the proximal catheter hub assembly 32 and to the distal end tip 34. The adjustable optical diversion element assembly 74 comprises an external switch 80 accessible from outside the convergence chamber 40, an optical actuator 82 and an optical dispersion element 84. When the external switch 80 is activated, it will engage the actuator 82 and align the optical dispersion element 84 to re-direct the EMR. This process of optical diversion may be either mechanical or electrical in nature.

Figure 9:
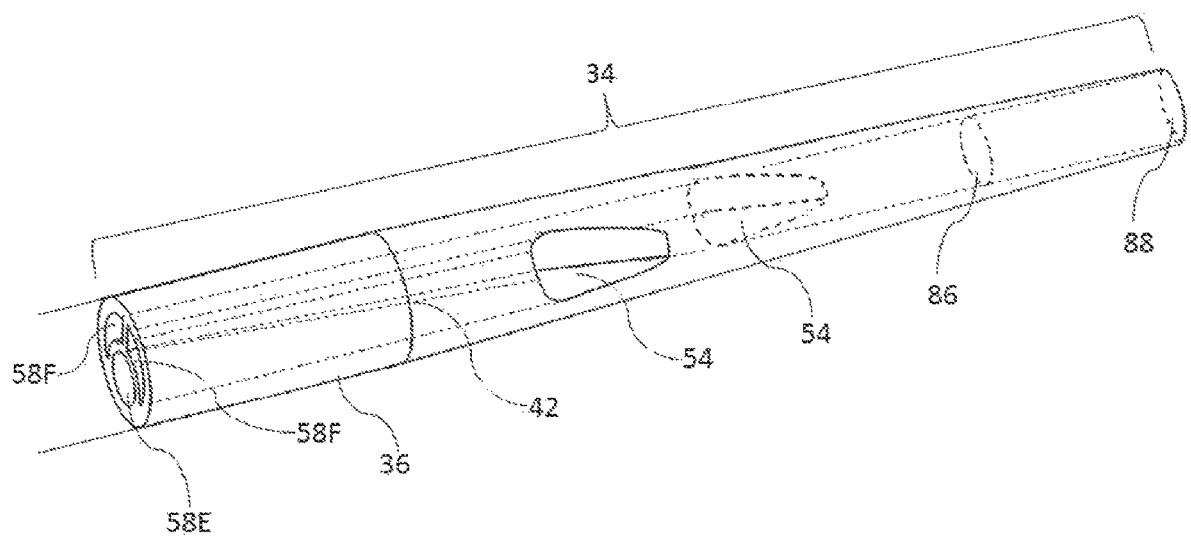
FIG. 9 is a perspective view of a distal end tip with internal configuration and phantom lines.

Referring now to FIG. 9, a distal end tip 34 being insertable into a patient's body is shown. The distal end tip 34 comprises an elongate catheter body 36, at least one internal lumen 30 capable of substantial axial transmission of an EMR element 58E and fluid element 58F or combination thereof, an optical element termination point 42, a distal end tip fluid exposure site 54, a fixed optical dispersion element 86. As EMR and fluid travel axially through the elongate catheter body 36. The fluid is able to exit or enter at the distal end tip fluid exposure site 54 depending on its needs. Distal from the optical element termination point 42 the EMR will become dispersed by the fixed optical dispersion element 86 and irradiate throughout the distal end tip 34 and surrounding cavity area.

Any methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention. Embodiments of the invention in which an exclusive property or privilege is claimed are defined as follows.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A coupling adapter for converging multiple sources into a catheter, at least one of the sources being an EMR source having a coupling element and being connected to an optical element that facilitates the propagation of EMR through at least a portion of the catheter, the coupling adapter comprising:
   a plurality of couplings, each coupling for connecting to one of the sources, at least one of the couplings being an EMR receiving coupling for connecting to the coupling element of the EMR source;
   a plurality of internal lumens, each internal lumen of the plurality of internal lumens is connected to one of the plurality of couplings, at least one of the internal lumens is connected to the EMR receiving coupling, receives a sterilizing EMR element, and is conducive to the propagation of EMR;
   a convergence chamber, each internal lumen of the plurality of internal lumens communicates with the convergence chamber, the convergence chamber being connected to the catheter, the convergence chamber receiving EMR from the EMR source for communication with the optical element to facilitate the propagation of EMR through at least a portion of the catheter; and
   wherein the convergence chamber further comprises an adjustable optical diversion element assembly for redirecting the EMR into at least one of the catheter, at least one of the internal lumens, and the coupling adapter.

2. The coupling adapter of claim 1, wherein the EMR receiving coupling communicates with the optical element to enhance axial propagation of the EMR.

3. The coupling adapter of claim 1, wherein the catheter is configured for access to at least one venous, arterial, gastrointestinal, urological, respiratory, cranial or spinal cavity.

4. The coupling adapter of claim 1, wherein at least one of the plurality of couplings is a fluid receiving coupling and at least one of the plurality of internal lumens is a fluid internal lumen, the fluid receiving coupling being connected to the fluid internal lumen.

5. The coupling adapter of claim 4, wherein the fluid internal lumen is conducive to at least one of an injection of fluid into the catheter and the removal of fluid from the catheter.

6. The coupling adapter of claim 5, wherein at least one of the injection of fluid into the catheter and the removal of fluid from the catheter is performable simultaneously with the propagation of EMR into the catheter.

7. The coupling adapter of claim 4, wherein the fluid internal lumen is conducive to the injection of fluid into the catheter, the injected fluid for inflating a balloon.

* * * * *